(12) United States Patent
Schumacher et al.

(10) Patent No.: US 9,821,130 B2
(45) Date of Patent: Nov. 21, 2017

(54) MULTI-DIAMETER PEDIATRIC TRACHEAL CUFF

(75) Inventors: James F. Schumacher, Cumming, GA (US); David W. Johnson, Milton, GA (US)

(73) Assignee: Avent, Inc., Alpharetta, GA (US)

( * ) Notice: Subject to any disclaimer, the term of this patent is extended or adjusted under 35 U.S.C. 154(b) by 874 days.

(21) Appl. No.: 13/314,267

(22) Filed: Dec. 8, 2011

(65) Prior Publication Data

US 2013/0146062 A1   Jun. 13, 2013

(51) Int. Cl.
*A61M 16/04* (2006.01)

(52) U.S. Cl.
CPC ........ *A61M 16/04* (2013.01); *A61M 16/0443* (2014.02); *A61M 16/0445* (2014.02)

(58) Field of Classification Search
CPC .............. A61M 25/10; A61M 16/0459; A61M 16/0438; A61M 16/0486; A61M 16/04; A61M 25/1006; A61M 16/0465; A61M 2025/1004; A61M 16/0445; A61M 16/0443; A61M 16/0434
USPC .......................... 128/207.15, 207.14, 200.26
See application file for complete search history.

(56) References Cited

U.S. PATENT DOCUMENTS

| | | | |
|---|---|---|---|
| 3,638,655 A * | 2/1972 | Doherty | A61M 25/04 128/207.15 |
| 4,130,617 A * | 12/1978 | Wallace | A61M 25/1029 264/528 |
| 4,502,482 A | 3/1985 | DeLuccia et al. | |
| 4,688,568 A | 8/1987 | Frass et al. | |
| 5,033,466 A * | 7/1991 | Weymuller, Jr. | A61M 16/0436 128/200.26 |
| 5,188,592 A | 2/1993 | Hakki | |
| 5,697,365 A | 12/1997 | Pell | |
| 6,062,223 A * | 5/2000 | Palazzo | A61M 16/04 128/207.14 |
| 6,266,548 B1 * | 7/2001 | Lamade | A61B 5/0421 600/375 |
| 6,287,290 B1 | 9/2001 | Perkins et al. | |
| 6,526,977 B1 | 3/2003 | Goebel | |
| 6,745,773 B1 * | 6/2004 | Gobel | A61M 16/04 128/204.18 |
| 6,843,250 B2 | 1/2005 | Efrati | |

(Continued)

FOREIGN PATENT DOCUMENTS

CN    201020135    2/2008
DE    198 45 415   9/1999

(Continued)

OTHER PUBLICATIONS

Connie Taylor, MD, et al., Pediatric Cuffed Endotracheal Tubes: An Evolution of Care, The Ochsner Journal 11, pp. 52-56 , 2011.

*Primary Examiner* — Kathryn E Ditmer
(74) *Attorney, Agent, or Firm* — Dority & Manning, P.A.

(57) ABSTRACT

The present disclosure describes an endotracheal tube for a child, the tube having a balloon mounted near the distal end of the tube. The tube has a ventilation lumen and an inflation line used to inflate the balloon. The balloon is mounted to the tube at a lower mounting point and an upper mounting point. The upper mounting point is above the level of the vocal cords. The balloon has a lower and upper diameter when inflated, and the upper diameter is from 1.1 to 1.5 times larger than the outer diameter of the tube.

20 Claims, 1 Drawing Sheet

(56) References Cited

U.S. PATENT DOCUMENTS

| | | | |
|---|---|---|---|
| 7,849,857 | B2 | 12/2010 | Goebel |
| 8,291,768 | B2 * | 10/2012 | Spiegel ............... A61M 16/044 604/121 |
| 8,333,795 | B2 * | 12/2012 | Weber ..................... A61F 2/856 604/103.07 |
| 8,820,319 | B2 | 9/2014 | Schwartz et al. |
| 2003/0000526 | A1 | 1/2003 | Gobel |
| 2003/0028211 | A1 * | 2/2003 | Crocker ................... A61F 2/86 606/192 |
| 2003/0066532 | A1 * | 4/2003 | Gobel ...................... 128/207.15 |
| 2003/0226566 | A1 | 12/2003 | Dhuper et al. |
| 2004/0116898 | A1 * | 6/2004 | Hawk ................... A61M 16/04 604/509 |
| 2008/0156323 | A1 | 7/2008 | Angel et al. |
| 2014/0251339 | A1 | 9/2014 | Pacey |

FOREIGN PATENT DOCUMENTS

| | | |
|---|---|---|
| EP | 1 005 877 A2 | 6/2000 |
| WO | WO 01/34221 | 5/2001 |
| WO | WO 2010/091440 A2 | 8/2010 |

\* cited by examiner

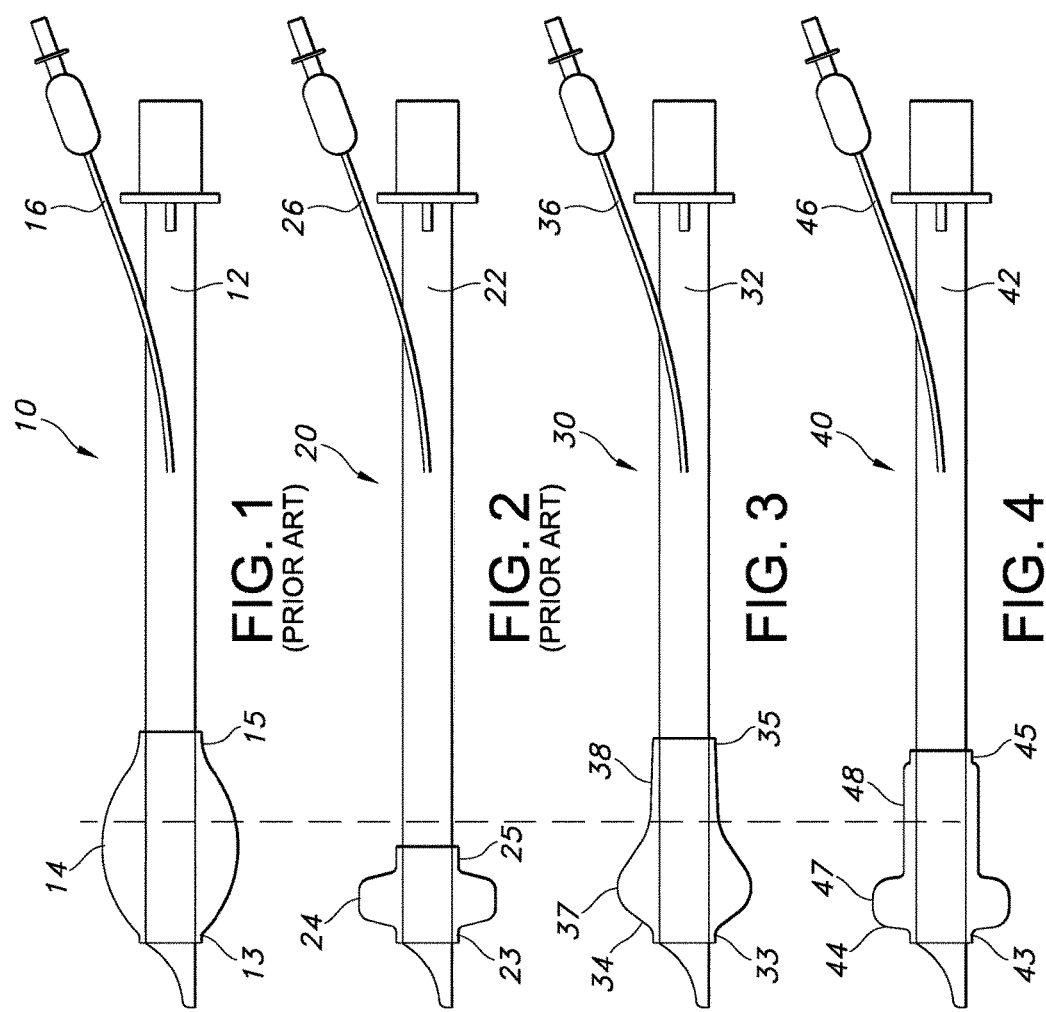

MULTI-DIAMETER PEDIATRIC TRACHEAL CUFF

BACKGROUND

The present disclosure relates to a cuff of balloon for an endotracheal tube for use with pediatric patients.

In the medical community it is well known that children are not merely small adults. Drugs, for example, may have no effect or the opposite effect on a child while being highly effective for an adult. Likewise, pediatric anatomy is quite different from that of adults. The distance from the vocal cords to the mouth is different than that of adults and the tissues of the throat, fragile and sensitive as they are in adults, are even more so in children.

Conventional tracheal tubes typically have a tube that serves as an artificial passage for the exchange of air between a patient and an air source, typically either atmospheric air or a mechanical respirator or ventilator. The distal end of the tube is usually equipped with a small, inflatable balloon, also called a cuff, which can be filled with a fluid (e.g., air). The balloon adheres to the internal lining of the trachea in its generally cross-sectional dimension in order to prevent air insufflated by the respirator into a patient from escaping to the environment through the larynx and pharynx. This enables the air to reach the lower airways and eventually the pulmonary alveoli. The balloon also aids in supporting the tube inside the trachea.

Pediatric tracheal tubes without sealing cuff balloons are available but are disadvantageous for ventilation in many cases, however. Surgery is especially problematic, requiring very constant maintenance of anesthesia (stable ventilatory minute volume) and constant blood gas levels, as is potentially the case, for example, with cardiac or neurosurgical intraoperative ventilation. During intensive care ventilation, spontaneous changes in the position of the child can be associated with sharply fluctuating air leaks and render stable ventilation impossible despite close vigilance. A cuffed tube is also sometimes preferred in heavily bleeding interventions in the head region or in intraoperative antiseptic irrigation of the buccal and pharyngeal cavities, due to the inadequate sealing efficiency of a cuffless tube. Blood, flushed-out debris and secretions from the throat will otherwise find their way largely unimpeded into the distal airways and can significantly complicate the ventilatory course and the course during and immediately after extubation.

Adapting an adult endotracheal tube for use in children has proven to be surprisingly difficult. One solution to this problem has been provided by Fred Gobel in U.S. Pat. No. 7,849,857 in which specific dimensions are given. These dimensions place the upper point for mounting the balloon to the tube below the level of the vocal cords in order to avoid damage. This solution works quite well. It would provide more flexibility for the medical professional and for manufacturing, however, if there were a balloon that could be mounted such that the upper point of attachment of the balloon to the tube is within the area of the vocal cords when in use, yet still avoid damage to the vocal cords.

What is needed is a balloon that may be mounted to a tracheal tube at a point such that it will be within area occupied by the vocal cords when the tube is in use.

SUMMARY

There is provided an endotracheal tube for a child, the tube having a balloon mounted near the distal end of the tube. The tube has a ventilation lumen and an inflation line used to inflate the balloon. The balloon is mounted to the tube at a lower mounting point and an upper mounting point. The upper mounting point is above the level of the vocal cords.

The balloon has a lower and upper diameter when it is inflated, the lower diameter is below the vocal cords and the upper diameter falling within the level of the vocal cords. The upper diameter is from 1.1 to 1.5 times larger than the outer diameter of the tube. The upper diameter may also be from 1.2 to 1.4 times the outer diameter of the tube.

The lower diameter is at least equal to the tracheal diameter below the vocal cords. The lower diameter may also be from 1.1 to 1.8 times the tracheal diameter below the vocal cords or more particularly from 1.3 to 1.6 times the tracheal diameter below the vocal cords.

The balloon may be made from a polymer selected from the group consisting of thermoplastic polyurethane polymers, thermoplastic polyolefin elastomers, thermoplastic polyolefin block copolymers, SBS di-block elastomers, SEBS tri-block elastomers, polyvinyl chloride (PVC), polyethylene terephthalate (PET) and blends and mixtures thereof.

The balloon may have a thickness of between 1 and 25 microns, more desirably between 5 and 15 microns. The balloon has an inflation pressure of between 5 and 30 mmH$_2$O, more desirably between 15 and 25 mmH$_2$O.

Other objects, advantages and applications of the present disclosure will be made clear by the following detailed description of a preferred embodiment of the disclosure and the accompanying drawings wherein reference numerals refer to like or equivalent structures.

BRIEF DESCRIPTION OF THE DRAWINGS

FIG. 1 is a drawing of a conventional pediatric endotracheal tube having a cuffed balloon that can damage the vocal cords of a child. The balloon expands in the region encompassing the vocal cords (dashed line).

FIG. 2 is a drawing of a pediatric endotracheal tube according to the teachings of U.S. Pat. No. 7,849,857. The balloon upper mounting point is below the region of the vocal cords.

FIG. 3 is a drawing of a pediatric endotracheal tube according to the teachings herein. The balloon upper mounting point is within the region of the vocal cords yet the balloon does not expand in this area.

FIG. 4 is a drawing of another embodiment of a pediatric endotracheal tube having a balloon having two distinct diameters, a larger one toward the distal end and a smaller one toward the proximal end of the balloon.

DETAILED DESCRIPTION

Reference will now be made to the drawings in which the various elements of the present disclosure will be given numeral designations and in which the disclosure will be discussed so as to enable one skilled in the art to make and use the disclosure. It is to be understood that the following description is only exemplary of the principles of the present disclosure, and should not be viewed as narrowing the pending claims. Those skilled in the art will appreciate that aspects of the various embodiments discussed may be interchanged and modified without departing from the scope and spirit of the disclosure.

FIG. 1 is a drawing of a prior art endotracheal tube 10 for a child. The tube 12 has a balloon 14 mounted near its distal end. It also has an inflation line 16 used to inflate the balloon 14. The balloon 14 is mounted to the tube 12 at a lower (distal) mounting point 13 and an upper (proximal) mounting point 15. The dashed line shows the approximate level of the vocal cords. As can be seen from the drawing, the balloon 14 of the prior art expands within the area of the vocal cords. Expanding the balloon in this area can damage the vocal cords and so is to be avoided if possible.

FIG. 2 is a drawing of an endotracheal tube 20 for a child made according to U.S. Pat. No. 7,849,857. The tube 22 has a ventilating lumen (not shown) that runs the entire length of the tube 22 in order to deliver breathing air to the patient. The tube 22 has a balloon 24 mounted near its distal end. It also has an inflation line 26 in fluid communication with and used to inflate the balloon 24 in the conventional manner. The balloon 24 is mounted to the tube 22 at a lower (distal) mounting point 23 and an upper (proximal) mounting point 25. The dashed line shows the approximate level of the vocal cords. As can be seen from the drawing, the balloon 24 according to U.S. Pat. No. 7,849,857 has an upper mounting point 25 below the level of the vocal cords and so expands in the area below the level of the vocal cords, avoiding damage to them.

The balloon according to the teachings herein is designed to have two diameters when inflated; an upper diameter and a lower diameter. This dual diameter balloon has an upper diameter (in the region of the vocal cords) that is smaller than the lower diameter (below the vocal cords). The largest diameter in each of the two regions (not an average) is the key dimension to be used herein. In some embodiments, the upper diameter when inflated can be just slightly larger than the tube itself in the area of the vocal cords, which will vary based on the size of the child. A desirable range for the upper diameter is from 1.1 to 1.5 times larger than the outer diameter of the tube to which the balloon is mounted. More desirably the upper diameter may be from 1.2 to 1.4 times the outer diameter of the tube to which the balloon is mounted. The lower diameter should have an inflated size that is at least equal to the tracheal diameter, which of course will vary based on the size of the child. More particularly, the lower diameter can be the same or larger than the tracheal diameter; e.g. from 1 to 2 times the tracheal diameter at the area below the vocal cords. More desirably the lower diameter may be from 1.1 to 1.8 times the tracheal diameter at the area below the vocal cords and still more desirably from about 1.3 to 1.6 times the tracheal diameter at the area below the vocal cords. The balloon is firmly attached, preferably by adhesive bonding or welding, on the distal portion of the tube, as illustrated.

FIG. 3 is a drawing of an embodiment of an endotracheal tube 30 for a child made according to the teachings herein. The tube 32 has a balloon 34 mounted near its distal end. It also has an inflation line 36 used to inflate the balloon 34 in the conventional manner. The balloon 34 is mounted to the tube 32 at a lower (distal) mounting point 33 and an upper (proximal) mounting point 35. The dashed line shows the approximate level of the vocal cords. As can be seen from the drawing, the balloon 34 according to these teachings expands in the area below the level of the vocal cords, avoiding damage to them, while having an upper mounting point 35 above the level of the vocal cords. The balloon thus has two diameters, one in the region of the vocal cords (the upper diameter 38) and one below the vocal cords (the lower diameter 37). The transition between the two diameters of this balloon is relatively gradual, as in a taper.

FIG. 4 shows another embodiment of the pediatric tube having a balloon 34 with two distinct diameters that change relatively abruptly (within less than 5 mm, desirably less than 3 mm) from one diameter to another. The upper (proximal) diameter 48 is only slightly larger than the tube but the diameter below the vocal cords, i.e. the lower diameter 47, is larger than the tracheal diameter as discussed above. The length of each of the distinct diameters is not critical to the functioning of the balloon except that it is important that the lower diameter continue for a distance sufficient to provide a seal against the tracheal wall and distribute the force of the expanded balloon. The length of the lower diameter parallel with the tube should therefore be at least 5 mm, desirably 10 mm except for the smallest sizes in which such a distance is impractical.

The table below shows an exemplary range for various parameters according to embodiments of the teachings herein. Referring to FIG. 4, the tube may have for example, using the first line of the table; a tube inner diameter of 3 mm and an outer diameter of 4.3 mm. Children at this age (0-1 years) usually have an internal transverse tracheal diameter of about 7 mm (see table) The distance from the distal tip to the distal mounting point of the balloon may be from 5 to 7 mm. The balloon has a diameter below the vocal cords of about 10 mm and maintains this diameter for a length of 7 to 9 mm. The balloon has an upper diameter (within the vocal cords) of from 1.1 times the outer tube diameter to about 1.5 times the outer tube diameter and maintains this diameter for a length of about 8 mm. The distance from the distal tip of the tube to the upper mounting point may be between 18 and 24 mm. The data in this table is meant to be exemplary only and not intended to limit the embodiments or scope of the invention.

| Tube ID Size (mm) | Tube OD Size (mm) | Intended Age Group (years) | Internal transverse tracheal diameter (mm) | Tube Tip to Distal Mounting Point of Cuff (mm) | Lower Cuff Diameter (mm) | Length of Lower Cuff Diameter (mm) | Range for Upper Cuff Diameter (mm) | Length of Upper Cuff Diameter (mm) | Tube Tip to Proximal Mounting Point of Cuff (mm) |
|---|---|---|---|---|---|---|---|---|---|
| 3.0 | 4.3 | 0-1 | 6.87 ± 0.78 | 5-7 | 10 | 7-9 | Min = 1.2*(Tube OD) | 8 | 18-24 |
| 3.5 | 5.0 | 1-2 | 7.20 ± 0.84 | 6-8 | 12 | 9-12 | Max = 1.5*(Tube OD) | 10 | 26-30 |
| 4.0 | 5.6 | 2-4 | 8.53 ± 1.07 | 7-10 | 12 | 9-13 | | 10 | 26-32 |
| 4.5 | 6.3 | 4-6 | 9.67 ± 1.50 | 8-11 | 14 | 12-15 | | 14 | 34-40 |
| 5.0 | 6.7 | 6-8 | 11.00 ± 1.52 | 10-12 | 14 | 12-15 | | 14 | 35-41 |
| 5.5 | 7.3 | 8-10 | 12.02 ± 1.85 | 11-13 | 16 | 14-18 | | 16 | 41-47 |
| 6.0 | 8.0 | 10-12 | 14.23 ± 2.00 | 12-15 | 18 | 14-18 | | 16 | 42-49 |
| 6.5 | 8.7 | 12-14 | 14.14 ± 2.36 | 13-16 | 20 | 19-23 | | 20 | 52-59 |
| 7.0 | 9.3 | 14-16 | 15.83 ± 2.16 | 14-17 | 20 | 19-23 | | 20 | 53-60 |

In the desired embodiments, the balloon is preferably fashioned of thin films that may be deigned to be high-volume/low-pressure cuffs. In these embodiments, the diameter of the balloon in the freely deployed, non-intubated state appreciably exceeds the diameter of the trachea to be intubated as noted above. An exemplary safety tolerance is usually about 50%. When a high-volume/low-pressure cuff is used to seal the trachea, due to the deployment of the cuff envelope that occurs in the trachea to occlude it, there is virtually no expansion of the cuff envelope under the potentially tissue-damaging pressures that are common with low-volume/high-pressure cuff balloons. This results in an intentionally produced folding of the balloon envelope and permits filling pressures that are compatible with perfusion. This provides the user with the certainty that the barometric pressure measured in the cuff balloon largely matches the pressure transmitted transmurally to the tissue. In the intubation of adults, severe tracheal or laryngeal injuries have been successfully reduced to a very low level, even with long-term intubation, through the use of such high-volume cuff balloons with a cuff envelope that is folded in situ. Further discussion of high-volume balloons may be found in, for example, U.S. Pat. Nos. 6,802,317 and 6,526,977, which teach oversized balloons with a wall thickness so low that the balloon walls lie in folds against the tracheal wall and the folds are so small that secretions cannot pass through them and travel on to the lungs.

U.S. Pat. No. 6,802,317 describes a cuff for obdurating a patient's trachea as hermetically as possible, comprising a cuffed balloon which blocks the trachea below a patient's glottis, an air tube, the cuffed balloon being attached to the air tube and being sized to be larger than a tracheal diameter when in a fully inflated state and being made of a soft, flexible foil material that forms at least one draped fold in the cuffed balloon when inflated in the patient's trachea, wherein the foil has a wall thickness below or equal to 0.01 mm and the at least one draped fold has a loop found at a dead end of the at least one draped fold, that loop having a small diameter which inhibits a free flow of secretions through the loop of the at least one draped fold.

U.S. Pat. No. 6,526,977 teaches a dilator for obdurating a patient's trachea as hermetically as possible, comprising a cuffed balloon which blocks the trachea below a patient's glottis, an air tube, the cuffed balloon being attached to the air tube and being sized to be larger than a tracheal diameter when in a fully inflated state and being made of a sufficiently soft, flexible foil material that forms at least one draped fold in the cuffed balloon when fully inflated in the patient's trachea, wherein the at least one draped fold formed has a capillary size which arrests free flow of secretions across the balloon by virtue of capillary forces formed within the fold to prevent aspiration of the secretions and subsequent infections related to secretion aspiration.

Polymers suitable for the production of the tracheal tube include polyvinyl chloride, polyurethane and polyolefins like polyethylene and polypropylene. Nylons and polyethylene terephthalate (PET) materials may also be used, though their cost may be prohibitive. Blends of suitable polymers may also be used. It is also possible using known extrusion techniques to extrude parts of the trach tube from one polymer and other parts of the tracheal catheter from other polymers. For example, the ventilating lumen walls may be made of a first polymer like polyvinyl chloride and the flexible wall may be made from a second polymer like polyurethane. One particularly suitable polymer is a polyvinyl chloride commercially available from Colorite Polymers Inc. as 8566G-015.

In the practice of the disclosed technology, the balloon component may be formed from thermoplastic polyurethane polymers, thermoplastic polyolefin elastomers, thermoplastic polyolefin block copolymers, SBS di-block elastomers, SEBS tri-block elastomers, polyvinyl chloride (PVC), polyethylene terephthalate (PET) and blends and mixtures thereof. More desirably, polyurethane may be used because it has been found to cause less irritation to tissues than other materials. Useful polyurethanes include those from the Dow Chemical Company (Dow Plastics) available under the tradename Pellethane®. Pellethane® thermoplastic polyurethane elastomer is available in a number of grades and hardnesses and the particular one selected for a specific use will depend on the properties desired in the final product. The hardness of a polymer, for example, is an attribute that may be varied to meet the requirements of various applications. One exemplary polyurethane is designated Pellethane® 2363-90A and has a durometer hardness of 90A (ASTM D-2240). This polyurethane has a softening temperature of 110° C. (ASTM D-790) and a melt index of 30 g/10 min. at 224° C., 2160 g (ASTM D-1238). The balloon is desirably very thin; with a thickness on the order of 25 microns or less, e.g. 20 microns, 15 microns, 10 microns or even as low as 5 microns in thickness, though at least 1 micron. The balloon should also desirably be a low pressure cuff operating at an inflation pressure of between 5 and 30 mmH$_2$O, more desirably between about 15 and 25 mmH$_2$O.

As used herein and in the claims, the term "comprising" is inclusive or open-ended and does not exclude additional unrecited elements, compositional components, or method steps.

While various patents have been incorporated herein by reference, to the extent there is any inconsistency between incorporated material and that of the written specification, the written specification shall control. In addition, while the disclosure has been described in detail with respect to specific embodiments thereof, it will be apparent to those skilled in the art that various alterations, modifications and other changes may be made to the disclosure without departing from the spirit and scope of the present disclosure. It is therefore intended that the claims cover all such modifications, alterations and other changes encompassed by the appended claims.

What is claimed is:

1. An endotracheal tube for a child having a trachea with a diameter and vocal cords at a level in the trachea, comprising:
   a tube having an outer diameter on which is mounted a balloon near a distal end of said tube, an inflation line used to inflate said balloon,
   said balloon mounted to said tube at a lower mounting point and an upper mounting point, said upper mounting point adapted to be placed above the level of said vocal cords,
   said balloon being inflatable in a region of the vocal cords and in a region below the vocal cords such that the balloon has an inflated lower diameter in the region below the vocal cords and an inflated upper diameter in the region of the vocal cords,
   wherein said inflated upper diameter is smaller than said inflated lower diameter, the balloon tapering from the inflated upper diameter to the inflated lower diameter,
   wherein said inflated upper diameter is constant over an upper diameter length, the upper diameter length defined from said upper mounting point to the level of the vocal cords,
   wherein the inflated upper diameter is larger than the outer diameter of the tube and the inflated lower diameter is at least equal to the tracheal diameter below the vocal cords, and wherein the balloon is a high-volume/low-pressure cuff for sealing the trachea.

2. The endotracheal tube of claim 1, wherein the inflated upper diameter is from 1.2 to 1.4 times the outer diameter of the tube.

3. The endotracheal tube of claim 2, wherein the inflated lower diameter is from 1.1 to 1.8 times the tracheal diameter below the vocal cords.

4. The endotracheal tube of claim 2, wherein the inflated lower diameter is from 1.3 to 1.6 times the tracheal diameter below the vocal cords.

5. The endotracheal tube of claim 1, wherein said balloon is made from a polymer selected from the group consisting of thermoplastic polyurethane polymers, thermoplastic polyolefin elastomers, thermoplastic polyolefin block copolymers, SBS di-block elastomers, SEBS tri-block elastomers, polyvinyl chloride (PVC), polyethylene terephthalate (PET) and blends and mixtures thereof.

6. The endotracheal tube of claim 1, wherein said balloon has a thickness of between 1 and 25 microns.

7. The endotracheal tube of claim 1, wherein said balloon has a thickness of between 5 and 15 microns.

8. The endotracheal tube of claim 1, wherein said balloon has an inflation pressure of between 5 and 30 mmH$_2$O.

9. The endotracheal tube of claim 1, wherein said balloon has an inflation pressure of between 15 and 25 mmH$_2$O.

10. The endotracheal tube of claim 1, wherein the inflated lower diameter is maintained over a lower diameter length, wherein said lower diameter length is at least 5 mm and the upper diameter length is at least 5 mm.

11. The endotracheal tube of claim 1, wherein the inflated lower diameter is maintained over a lower diameter length, wherein said lower diameter length is approximately 10 mm and the upper diameter length is approximately 10 mm.

12. The endotracheal tube of claim 1, wherein said balloon changes from said inflated upper diameter to said inflated lower diameter within less than 5 mm.

13. The endotracheal tube of claim 1, wherein said balloon changes from said inflated upper diameter to said inflated lower diameter within less than 3 mm.

14. An endotracheal tube for a child having a trachea with a diameter and vocal cords at a level in the trachea, comprising:
    a tube having an outer diameter on which is mounted a balloon near a distal end of said tube, an inflation line used to inflate said balloon,
    said balloon mounted to said tube at a lower mounting point and an upper mounting point, said upper mounting point adapted to be placed above the level of said vocal cords,
    said balloon being inflatable in a region of the vocal cords and in a region below the vocal cords such that the balloon has an inflated lower diameter in the region below the vocal cords and an inflated diameter in the region of the vocal cords,
    wherein the balloon is a high-volume/low-pressure cuff for sealing the trachea that has an inflation pressure of no more than 30 mmH$_2$O,
    wherein said inflated upper diameter is smaller than said inflated lower diameter, said inflated upper diameter being constant over an upper diameter length, the upper diameter length defined from said upper mounting point to the level of the vocal cords,
    wherein the inflated upper diameter is larger than the outer diameter of the tube and the inflated lower diameter is at least equal to the tracheal diameter below the vocal cords, and
    wherein said inflated lower diameter is maintained for a lower diameter length, the lower diameter length being within a range of lengths having a minimum value of 5 mm.

15. The endotracheal tube of claim 14, wherein the lower diameter length is approximately 10 mm and the upper diameter length is approximately 10 mm.

16. The endotracheal tube of claim 14, wherein said balloon changes from said inflated upper diameter to said inflated lower diameter within less than 5 mm.

17. The endotracheal tube of claim 14, wherein said balloon changes from said inflated upper diameter to said inflated lower diameter within less than 3 mm.

18. An endotracheal tube for a child having a trachea with a diameter and vocal cords at a level in the trachea, comprising:
    a tube having an outer diameter on which is mounted a balloon near a distal end of said tube, an inflation line used to inflate said balloon,
    said balloon mounted to said tube at a lower mounting point and an upper mounting point, said upper mounting point adapted to be placed above the level of said vocal cords,
    said balloon being inflatable in a region of the vocal cords and in a region below the vocal cords such that the balloon has an inflated lower diameter in the region below the vocal cords and an inflated upper diameter in the region of the vocal cords,
    wherein the balloon is a high-volume/low-pressure cuff for sealing the trachea that has an inflation pressure of no more than 30 mmH$_2$O,
    wherein said inflated upper diameter is smaller than said inflated lower diameter, said inflated upper diameter being constant over an upper diameter length, the upper diameter length defined from said upper mounting point to the level of the vocal cords,
    wherein the inflated upper diameter is larger than the outer diameter of the tube and the inflated lower diameter is at least equal to the tracheal diameter below the vocal cords, and
    wherein said inflated lower diameter is maintained for a lower diameter length such that the lower diameter length and the upper diameter length are at least 5 mm.

19. The endotracheal tube of claim 18, wherein the lower diameter length is approximately 10 mm and the upper diameter length is approximately 10 mm.

20. The endotracheal tube of claim 18, wherein said balloon changes from said inflated upper diameter to said inflated lower diameter within less than 5 mm.

* * * * *